(12) United States Patent
Ohl et al.

(10) Patent No.: US 6,395,963 B1
(45) Date of Patent: May 28, 2002

(54) NEMATODE-INDUCIBLE REGULATORY DNA SEQUENCES

(75) Inventors: Stephan Andreas Ohl, Leiden; Peter Christiaan Sijmons, Amsterdam; Frédérique Marianne Klein-Van der Lee, Delft; Oscar Goddijn, Leiden; Joke Klap, Arnheim, all of (NL)

(73) Assignee: Zeneca Limited, London (GB)

( * ) Notice: Subject to any disclaimer, the term of this patent is extended or adjusted under 35 U.S.C. 154(b) by 0 days.

(21) Appl. No.: 09/308,090

(22) PCT Filed: Nov. 18, 1997

(86) PCT No.: PCT/EP97/06472

§ 371 (c)(1),
(2), (4) Date: May 17, 1999

(87) PCT Pub. No.: WO98/22599

PCT Pub. Date: May 28, 1998

(30) Foreign Application Priority Data

Nov. 18, 1996 (EP) .............................. 96203213

(51) Int. Cl.⁷ .................. C12N 15/29; C12N 15/31; C12N 15/82; C12N 5/00; A01H 5/00
(52) U.S. Cl. .................. 800/279; 800/278; 800/294; 800/298; 800/306; 800/286; 800/287; 800/288; 800/317.2; 435/69.1; 435/468; 435/419; 435/252.3; 435/320.1; 435/199; 435/6; 536/23.1; 536/24.1; 536/23.71; 536/23.6; 536/23.7; 536/24.5; 47/6
(58) Field of Search .................. 800/278, 279, 800/294, 298, 306, 286, 287, 288, 317.2; 435/69.1, 468, 419, 252.3, 320.1, 199, 6; 536/23.1, 24.1, 23.71, 23.6, 23.7, 24.5; 47/6

(56) References Cited

FOREIGN PATENT DOCUMENTS

| WO | WO 92/21757 | 12/1992 |
|----|-------------|---------|
| WO | WO 93/06710 | 4/1993 |
| WO | WO 93/10251 | 5/1993 |
| WO | WO 94/10320 | 5/1994 |
| WO | WO 95/3228 | 11/1995 |
| WO | WO 97/20057 | 6/1997 |
| WO | WO 97/46692 | 12/1997 |

OTHER PUBLICATIONS

Kim et al. Plant Molecular Biology, vol. 24, pp. 105–117, 1994.*
EMBL acc. No. U02426: Cloning vector lambda EMBL3 SP6/T7, left arm. (Paper copy of database entry).
EMBL acc. No. Z24516: *A. thaliana* transcribed sequence; clone RaR091; 5'end (Paper copy of database entry).
Barthels, N. et al., The Plant Cell, vol. 9, 2119–2134, 1997.
Sijmons, P.C. et al., Advances in Molecular Genetics, vol. 3, 333–338, 1994.
Goddijn, O. et al., The Plant Journal, vol. 5, 863–873, 1993.

* cited by examiner

*Primary Examiner*—Phuong T. Bui
*Assistant Examiner*—Medina A. Ibrahim
(74) *Attorney, Agent, or Firm*—Hale and Dorr LLP

(57) ABSTRACT

Nematode-inducible promoter sequences are disclosed. These sequences can be used for expressing DNA sequences in plant cells. Chimeric DNA constructs comprising the nematode-inducible promoter sequences operably linked to DNA to be expressed in plant cells are also disclosed. Plants comprising the chimeric DNA are provided. Methods for making plants that are resistant to plant parasitic nematodes are

21 Claims, 6 Drawing Sheets

NFS-disruptive gene

Promoter type-A　　　　　　　　　　　　　　　terminator
(active in NFS)

Neutralizing gene

Promoter type-B　　　　　　　　　　　　　　　terminator
(active outside NFS)

SEQUENCE LISTING

```
<160> NUMBER OF SEQ ID NOS: 10

<210> SEQ ID NO 1
<211> LENGTH: 3484
<212> TYPE: DNA
<213> ORGANISM: Arabidopsis thaliana
<220> FEATURE:
<221> NAME/KEY: CDS
<222> LOCATION: (3482)..(3484)

<400> SEQUENCE: 1
aagctagatc tagactcgag aagcttggat ccccgggtat atgaaagaga cgaccactgc      60
cagggacgaa agtgcaatgc gcatacctca gtggcgtgga gtgcaggtat acagattaat     120
ccggcagcgt ccgtcgttgt tgatattgct tatgaaggct ccggcagtgg cgactggcgt     180
actgacggat tcatcgttgg ggtcggttat aaattctgat tagccaggta acacagtgtt     240
atgacagccc gccggaaccg gtgcggtttt ttgtggggtg aatatgcagt aaagatttca     300
ggagtcctga aagacggcac aggaaaaccg gtacagaact gcaccattca gctgaaagcc     360
agacgtaaca gcaccacggt ggtggtgaac acggtgggct cagagaatcc ggatgaagcc     420 tgcttttta tactaagttg gcattataaa aaagcattgc ttatcaattt gttgcaacga     480
acaggtcact atcagtcaaa ataaaatcat tatttgattt caattttgtc ccactccctg     540
cctctgtcat cacgatactg tgatgccatg gtgtccgact tatgcccgag aagatgttga     600
gcaaacttat cgcttatctg cttctcatag agtctgcaga caaactgcgc aactcgtgaa     660
aggtaggcgg atctgggtcg actctaggcc tcactggcta atacgactca ctataggag     720 ctcgacttcc ctcaacatac tcatgtacgt aagattcact ctacatgttg acccatgcac     780
gtaccaagtt cttcatatac aagaatgaga tttaagtgaa cttctagatg agttaaaact     840
gaatattaca gaaacaacga caggagtttt ctctccaaat ctatgaattc tccgaagaaa     900
agattgagct gacatttgct acagcttttt ggtaattttg tggaattgac atgtgataca     960
tgaatatatc tatgtagagt gaaagaaaat taatgatggt tagcataact tttcaggaca    1020
ttactaaatg ctgatagaga aaatgataga tacggccgag aagagtggaa tcgaaggaag    1080
aatcattaac ctttcctctg tgattcacag ttgggtcaag cctgattgtt tctccttccc    1140
taacttactc catccattag gtaatctaca ttcgtttcat tttttacgcg tgaaagtatc    1200
taagaaaaaa ggtatctcaa aaatatattt atcattaggt ttatgtaatt aagtttaatt    1260
tgtaattgtg ttttgtaatc gtctagtagg tatacgggac aagggcatat gctcagtcaa    1320
agttggccac aattttacat gccaaagcct tgagcaagca attaaggta tatttcaaaa    1380 ttaataatta catctttctt ttttgtttaa ttttttttcac gtaaactaat aatcagaaat    1440
atttatcact gaatgtgctt acaggacaga aatgcaaacg tgacgataaa tgcagtccat    1500
ccaggaactg ttaaactgga attatcagag cacacaaggg tcttttttaca ggtaaaacaa    1560 aacttttttt tccatacata tatatagaaa tgcaaaagga atctaataag taagaaaaaa    1620
```

```
aaaatcctaa aaccattgat gtggttttca atgatatgca tatgcagatt ctctgctttt    1680
ttgcaatagc ttcgaaaatg cctgctaaaa tctataaaag ccaggaggtg tgaataatat    1740
atagccttac cttttaagct ctaaatagta caataaaggc ctaacagtca ttctctttag    1800
cctgacacta gattccttt tgtttcgttt tttgtatccc aaatcaaggt tttgtcatca    1860
tcaatattca tgcatagact catatacata catgccacta agaatcaaaa tttacgttga    1920
atgattgtac actttagatg atttttaatcg cctcttcttg caatttctgt ttcttcactt    1980
cttttagctc cttcttgctc tatttgcttt ccaaattcca tgttccactc cagatccta    2040 gaagtgagaa atgcaatgca acatgcacc taagcctaaa catgaatgca atgatgaaa    2100 ctaaaagagc gaagctaaaa accaaacaaa aacacagata tcagcaaact agacaaaata    2160
ataaatagtt tgttttttt gttgttgttg aaatagtgga tatattttg tgtttctaat    2220 attaattact atatcattta atcttataag tttttttggg ttaatttaag tgtaatttaa    2280
tatttcacat gtaacaagaa ctccatttta ttcttgtccg gttcttgaat aagatgtgaa    2340
agtattgtat caattgatga tgatgaatgc atgtgtgcta accatttacg ttatcttttt    2400
ttcacgataa ataaacgaaa gttgtttggt atgtgaacaa agaaatcaat ttcaaaatta    2460
ttttcaaaaa gtacaatttc ttccattgtt ttcacaataa gagaactaaa gttatttggt    2520
atgtgatctt ctatatataa aaaaaaaatc catcgtcgaa actaagattt tgttttcta    2580 tatatctttt aaaatgtaat aaatattagg taatatatg tttttctatt gtattttttt    2640
tttcaataac ctttactatt ttaaatctat ctgcaaatat tattttattt gaaaggtaaa    2700
aaattttgga tttagtattt gtcatatgat atctgattat ggttttcagg agccgattag    2760
atgtcacttt ttagtcattg gttttagctt tcatcaacgc ttttgaaaat tgaactcaaa    2820 ttatttggc ctaacttatg tcattcaact aaaagacatt acaataactg ttgtctaaag    2880
actaaagaaa gatcttaaat ttaagaaaga agatactatt tgtcaaaaga ggactaaaat    2940
gctaaatttc agaaagaaaa tgaaggaagg tggtgggaag tgtgtgtgat ttaacttgat    3000
attgggaaaa gcacgtaata acaactaagt taggagaaaa gtaagcaaaa aaaaaaaaag    3060
ataaacgcgg acacacacag ctaacacgca catcacatca ctacaaagag gatgcagtgt    3120
catgaattgc gtttgcttct aaaatctgta accgataatc catcttgttt cagaaaaata    3180
aatgtattcg ttcgccggct tgaattcgac gcgataaggc cgaggaaaga catcttgcta    3240
gacgctcttt gtttactata tagtcttaat tttggtggag taggtcggtg tgaataagga    3300
aatataaaag cctattgggt caagtaaggc ccaataatag attactgttt atataaaata    3360
ttactgttta tataagatat tagactaaac tttagtctaa tcagattata acatttttt    3420 tattttatc tcactcttct tcctcttcca aagcttggat ccccgggtag gtcagtccct    3480 t atg                                                               3484
  Met
   1
```

<210> SEQ ID NO 2
<211> LENGTH: 1
<212> TYPE: PRT
<213> ORGANISM: Arabidopsis thaliana

<400> SEQUENCE: 2

Met
 1

```
<210> SEQ ID NO 3
<211> LENGTH: 22
<212> TYPE: DNA
<213> ORGANISM: Artificial Sequence
<220> FEATURE:
<223> OTHER INFORMATION: Description of Artificial Sequence:primer

<400> SEQUENCE: 3
cggactctgg atccggaaag tg                                             22

<210> SEQ ID NO 4
<211> LENGTH: 36
<212> TYPE: DNA
<213> ORGANISM: Artificial Sequence
<220> FEATURE:
<223> OTHER INFORMATION: Description of Artificial Sequence:primer

<400> SEQUENCE: 4
ctgctcgagc ctaggcacag gttatcaaca cgtttg                              36

<210> SEQ ID NO 5
<211> LENGTH: 27
<212> TYPE: DNA
<213> ORGANISM: Artificial Sequence
<220> FEATURE:
<223> OTHER INFORMATION: Description of Artificial Sequence:primer

<400> SEQUENCE: 5
cttactcgag ccatggtaag tttctgc                                        27

<210> SEQ ID NO 6
<211> LENGTH: 44
<212> TYPE: DNA
<213> ORGANISM: Artificial Sequence
<220> FEATURE:
<223> OTHER INFORMATION: Description of Artificial Sequence:primer

<400> SEQUENCE: 6
gatctagact cgagaagctt ggatccccgg gtaggtcagt cccc                     44

<210> SEQ ID NO 7
<211> LENGTH: 44
<212> TYPE: DNA
<213> ORGANISM: Artificial Sequence
<220> FEATURE:
<223> OTHER INFORMATION: Description of Artificial Sequence:primer

<400> SEQUENCE: 7
catgggggac tgacctaccc ggggatccaa gcttctcgag tcta                     44

<210> SEQ ID NO 8
<211> LENGTH: 12
<212> TYPE: DNA
<213> ORGANISM: Artificial Sequence
<220> FEATURE:
<223> OTHER INFORMATION: Description of Artificial Sequence:adapter

<400> SEQUENCE: 8
agctcggatc cg                                                        12

<210> SEQ ID NO 9
<211> LENGTH: 12
<212> TYPE: DNA
<213> ORGANISM: Artificial Sequence
<220> FEATURE:
<223> OTHER INFORMATION: Description of Artificial Sequence:adapter
```

-continued

```
<400> SEQUENCE: 9
ggctgctcga gc                                                              12

<210> SEQ ID NO 10
<211> LENGTH: 18
<212> TYPE: DNA
<213> ORGANISM: Artificial Sequence
<220> FEATURE:
<223> OTHER INFORMATION: Description of Artificial Sequence:adapter

<400> SEQUENCE: 10
aattgacgaa gcttcgtc                                                        18
```

NEMATODE-INDUCIBLE REGULATORY DNA SEQUENCES

The invention relates to nematode-inducible regulatory DNA sequences which can be used for expressing DNA sequences in plant cells. The invention further comprises chimeric DNA comprising said regulatory DNA sequences operably linked to DNA to be expressed in plant cells, as well as plants containing such chimeric DNA in their cells. The invention further relates to methods for making plants that are resistant, or at least less susceptible to plant parasitic nematodes, or their effects, as well as to cells, plants and parts thereof.

STATE OF THE ART

In International patent application WO92/17054, a method is disclosed for the identification and subsequent isolation of nematode responsive regulatory DNA sequences from *Arabidopsis thaliana*.

In WO 92/21757 several regulatory DNA sequences have been isolated from *Lycopersicon esculentum*, which are responsive to the root-knot nematode *Meloidogyne incognita*. Some of these regulatory sequences (LEMMI's, for *Lycopersicon esculentum—Meloidogyne incognita*) are stimulated, whereas others appear to be repressed by the nematode. It is not known whether any of the inducible regulatory sequences are stimulated by a broader range of nematodes.

Another regulatory sequence that is inducible by the root-knot nematode *Meloidogyne incognita* is disclosed in WO 93/06710. A disadvantage of this regulatory sequence TobRb7 is that it is not activated by a number of cyst nematodes, among which the Heterodera and Globoelera species. This makes the TobRB7 sequence unsuitable for use in chimeric constructs aiming at, for example, cyst nematode resistance in potato.

It is an object of the invention to provide regulatory DNA sequences which are inducible by both cyst and root knot nematodes and which can be used to express heterologous DNA sequences under their control inside the feeding structure of the nematode, preferably, but not necessarily in a substantially feeding site specific way.

SUMMARY OF THE INVENTION

The invention provides a DNA fragment obtainable from *Arabidopsis thaliana* that is capable of promoting root knot and cyst nematode-inducible transcription of an associated DNA sequence when re-introduced into a plant. Preferred according to the invention are sequences represented by nucleotides 1 to 3484 in SEQIDNO: 1. Also envisaged are portions or variants of a DNA fragment according to the invention capable of promoting root knot and cyst nematode-inducible transcription of an associated DNA sequence when re-introduced into a plant. A still further preferred aspect of the invention comprises a regulatory DNA fragment that is substantially nematode feeding site-specific.

Further embodiments of the invention comprise chimeric DNA sequences comprising in the direction of transcription a regulatory DNA fragment according to the invention and a DNA sequence to be expressed under the transcriptional control thereof and which is not naturally under transcriptional control of said DNA fragment. Preferred among the chimeric DNA sequences according to the invention are those wherein the DNA sequence to be expressed causes the production of a plant cell-disruptive substance, such as barnase. In a different embodiment the cell-disruptive substance comprises RNA complementary to RNA essential to cell viability. Yet in another embodiment the DNA sequence to be expressed causes the production of a substance toxic to the inducing nematode.

The invention finds further use in a replicon comprising a DNA fragment or chimeric DNA sequence according to the invention, a microorganism containing such a replicon, as well as plant cells having incorporated into their genome a chimeric DNA sequence according to the invention. Further useful embodiments are a root system of a plant essentially consisting of cells according to the invention, as well as full grown plants essentially consisting of cells according to the invention, preferably a dicotyledonous plant, more preferably a potato plant. Also envisaged are plants grafted on a root system according to the invention, as well as plant parts selected from seeds, flowers, tubers, roots, leaves, fruits, pollen and wood and crops comprising such plants.

The invention also encompasses the use of a DNA fragment according to the invention for identifying subfragments capable of promoting transcription of an associated DNA sequence in a plant. Also envisaged is the use of a chimeric DNA sequence according to the invention for transforming plants. The invention further provides the use of a fragment, portion or variant of a regulatory DNA according to the invention for making hybrid regulatory DNA sequences.

The following figures further illustrate the invention.

Figure 1:
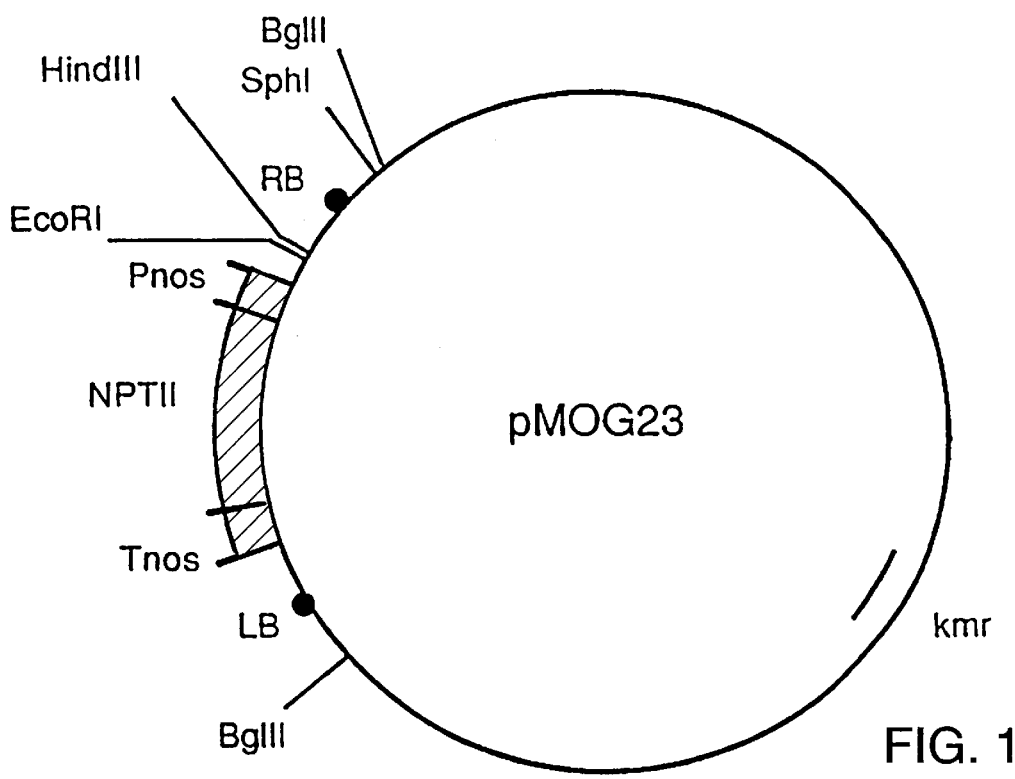
FIG. 1. Schematic plasmid map of Binary vector pMOG23.

Some ways of practicing the invention as well as the meaning of various phrases are explained in more detail below.

DETAILED DESCRIPTION OF THE INVENTION

The present invention provides regulatory DNA sequences obtainable from *Arabidopsis thaliana*, which are inducible by root knot and cyst nematodes and which show a high preference of expression of compounds coded for by any associated DNA inside the special nematode feeding structures of the plant root. A method of isolating regulatory DNA sequences has been disclosed and claimed in a prior application, WO92/17054, which is incorporated herein by reference.

In principle the regulatory DNA sequences according to the invention can be used to express any heterologous DNA in any plant of choice, by placing said DNA under the control of said regulatory DNA sequences and transforming plants with the resulting chimeric DNA sequence using known methods. The heterologous DNA is expressed upon infection of the roots by various root knot nematodes, such as *Meloidogyne incognita*, and cyst nematodes, such as *Heterodera schachtii* and *Globodera pallida* (a more comprehensive, but by no means limiting, list is presented in table 2). Advantageously, the heterologous DNA may consist of a gene coding for a substance that is toxic or inhibitive to a plant parasitic nematode in order to create plants with reduced susceptibility to plant parasitic nematodes. There exist numerous examples of such toxic substances, such as the endotoxins of *Bacillus thuringiensis* (e.g. EP 0 352 052), lectins, and the like.

A more preferred approach for making plants with reduced susceptibility to plant parasitic nematodes consists in the disruption of the specialised feeding structure of the plant roots by expressing a phytotoxic substance under the control of the regulatory DNA sequences according to the invention. The general principles of this approach have been disclosed and claimed in International patent applications WO92/21757, WO93/10251 and WO94/10320, which are hereby incorporated by reference. For the sake of consistency, the phytotoxic substance shall be referred to hereinafter as the nematode feedings site (NFS) disruptive substance.

Although the regulatory DNA sequences according to the invention are substantially specific for the nematode feeding structure, it may be that expression of NFS disruptive substances under the control thereof has adverse effects on plant viability and/or yield, due to expression in non-target (i.e. non-NFS) tissues. Moreover, it was found that the regulatory DNA sequences according to the invention are active during the tissue culture phase in the transformation procedure, necessitating the use of a neutralising substance during this phase. In order to reduce or eliminate (potential) adverse effects, it is therefore strongly preferred to use a chimeric NFS-disruptive construct according to the invention in conjunction with a neutralising gene construct. The details of such a so-called two-component approach for the engineering of nematode resistant plants are set out in WO93/10251. According to this approach a NFS-disrupter gene (gene-A) is placed under the control of a promoter that is at least active in the NFS, and preferably not or hardly outside the NFS, whereas the unwanted phytotoxic effects outside the NFS are neutralised by a neutralising gene (gene-B) that is expressed at least in those tissues wherein the disruptive substance is produced except for the NFS.

According to the two-component approach a suitable promoter-A is defined as a promoter that drives expression of a downstream gene coding for a disruptive substance inside the NFS, at levels sufficient to be detrimental to the metabolism and/or functioning and/or viability of the NFS, while this promoter should preferably, but not necessarily, be inactive in tissues outside the NFS; it should at least never be active outside NFS at such levels that the activity of the disruptive substance, encoded by gene-A, can not be neutralized sufficiently by products from gene-B.

The properties of the regulatory DNA sequences according to the invention, also indicated by the mnemonic #25.1, make them highly useful in the two-component approach, as is illustrated by way of Examples herein. Obviously, numerous mutations are possible in the regulatory DNA sequences according to the invention which do not alter the properties of these sequences in a way crucial to their intended use. Such mutations do, therefore, not depart from the present invention.

Moreover, as is well known to those of skill in the art, regulators regions of plant genes consist of distinct subregions with interesting properties in terms of gene expression. Examples of subregions as meant here, are enhancers but also silencers of transcription. These elements may work in a general (constitutive) way, or in a tissue-specific manner. Several deletions may be made in the regulatory DNA sequences according to the invention, and the subfragments may be tested for expression patterns of the associated DNA. Various subfragments so obtained, or even combinations thereof, may be useful in methods of engineering nematode resistance, or other applications involving the expression of heterologous DNA in plants. Functional subregions, and the subsequent use thereof to promote or suppress gene expression in plants are also encompassed by the present invention.

Within the context of this invention, the terms NFS disruptive substance and neutralizing substance embraces a series of selected compounds that are encoded by DNA whose gene products (either protein or RNA or antisense-RNA) are detrimental to the metabolism and/or functioning and/or viability of NFS or organelles therein and for which neutralizing substances are known that are able, when expressed simultaneously in the same cell as the disruptive substance, to repress the activity of the disrupting substance. Preferred combinations of disrupting and neutralizing substances are e.g. barnase/barstar from *Bacillus amyloliquefaciens* (Hartley, 1988, J. Mol. Biol. 202, 913–915), restriction endonucleases/corresponding methylases such as EcoRI from *E. coli* (Green et al., 1981, J. Biol. Chem. 256, 2143–2153) and EcoRI methylase or similar combinations as described in the review for type II restriction modification systems (Wilson, 1991, Nucl. Acid Res. 19, 2539–2566), bacteriocins and corresponding immunity proteins, e.g. colicin E3/immunity protein from *E. coli* (Lau et al. 1985, Nucl. Acid Res. 12, 8733–8745) or any disruptive substance coding gene which may be neutralized by simultaneous production of antisense RNA under control of promoter-B, such as DNA sequences encoding Diptheria Toxin Chain A (Czako & An, 1991, Plant Physiol. 95, 687–692), RNAses such as RNAse T1, ribonucleases or proteases. A further possibility is to have a gene coding for a ribozyme active against mRNA that code for phytotoxic protein.

According to another aspect of the invention combinations of disrupting and neutralizing substances comprise respectively genes inhibitory to an endogenous gene that encodes a protein or polypeptide product that is essential for cell viability and, as a neutralizing gene, a gene that encodes a protein or polypeptide product capable of substituting the function of the endogenous protein or polypeptide product. Such disruptive genes may be selected from the group consisting of (a) genes encoding ribozymes against an endogenous RNA transcript, (b) genes which when transcribed produce RNA transcripts that are complementary or at least partially complementary to RNA transcripts of endogenous genes that are essential for cell viability, a method known as antisense inhibition of gene expression (disclosed in EP-A 240 208), and (c) genes that when transcribed produce RNA transcripts that are identical or at least very similar to transcripts of endogenous genes that are essential for cell viability, an as yet unknown way of inhibition of gene expression referred to as co-suppression (disclosed by Napoli C. et al., 1990, The Plant Cell 2, 279–289).

According to a preferred embodiment of the invention use is made of antisense genes to inhibit expression of endogenous genes essential for cell viability, which genes are expressed in the nematode feeding structures by virtue of regulatory DNA sequences according to the invention fused upstream to the said antisense gene.

The disruptive effect brought about by the antisense gene inhibitory to the vital endogenous gene is neutralized by the expression of a neutralizing gene-B under the control of a promoter-B as defined, said gene-B when expressed produces a protein or polypeptide product which is identical or similar to the protein or polypeptide encoded by the endogenous vital gene and capable of substituting the function of the endogenous gene product in the host plant. It is preferred that the nucleotide sequence of the RNA transcript encoded by the neutralizing gene is divergent from the endogenous vital gene RNA transcript to avoid a possible co-suppressive effect. Hence, it is preferred that the neutralizing gene encodes a protein or polypeptide with essentially the same function as the endogenous vital gene, but through an RNA transcript intermediate that is divergent; neutralizing genes which fit this description can be suitably obtained by screening a database for genes obtainable from a different plant species, or even a different non-plant species, such as yeasts, animal eukaryotes or prokaryotes. Preferably, the nucleotide sequence identity of the transcripts encoded by the disruptive antisense transgene and the neutralizing sense transgene is less than 90%, preferably less than 80%, yet more preferably said neutralizing sense transgene encodes a protein or polypeptide gene product that is not identical in amino acid sequence to the disrupted gene product and wherein the nucleotide sequence identity of the transcripts encoded by the neutralizing transgene is less than 75%.

Target genes for antisense disrupter genes are selected from those coding for enzymes that are essential for cell viability, also called housekeeping enzymes, and should be nuclear encoded, preferably as single copy genes, although a small size gene family would also be suitable for the purpose of the invention. Furthermore, the effect of antisense expression of said genes must not be nullified by diffusion or translocation from other cells or organelles of enzyme products normally synthesized by such enzymes. Preferably, genes coding for membrane-translocating enzymes are chosen as these are involved in establishing chemical gradients across organellar membranes. Inhibition of such proteins by antisense expression can not, by definition, be cancelled by diffusion of substrates across the membrane in which these proteins reside. The translocated compound is not limited to organic molecules but can be of inorganic nature; e.g. P, H, OH or electrons.

Preferably, the membrane-translocating enzymes should be present in organelles that increase in numbers during parasitism, thereby illustrating the essential role that such organelles have in cells comprising the NFS. Specific examples for such organelles are mitochondria, endoplasmic reticulum and plasmodesmata (Hussey et al. 1992 Protoplasma 167; 55–65, Magnusson & Golinowski 1991 Can. J. Botany 69; 44–52). A list of target enzymes is given in Table 1 by way of example but the invention is not limited to the enzymes mentioned in this table. More detailed listings can be assembled from series as Biochemistry of Plants (Eds. Stumpf & Conn, 1988–1991, Vols. 1–16 Academic Press) or Encyclopedia of Plant Physiology (New Series, 1976, Springer-Jerlag, Berlin).

Although only in some cases, the genes coding for these enzymes have been isolated and, therefore, the number of gene copies is not known generally, the criteria that have to be met are described in this invention.

TABLE 1

Examples of target enzymes for antisense expression in NFS

| enzyme | pathway/organelle |
| --- | --- |
| ATP synthase | mitochondrion |
| adenine nucleotide translocator | mitochondrion |
| phosphate translocator | mitochondrion |
| tricarboxylate translocator | mitochondrion |
| dicarboxylate translocator | mitochondrion |
| 2-oxo-glutarate translocator | mitochondrion |
| cytochrome C | mitochondrion |
| pyruvate kinase | glycolysis |
| glyceraldehyde-3P-dehydrogenase | glycolysis |
| NADPH-cytochrome P450 reductase | lipid metabolism |
| fatty acid synthase complex | lipid metabolism |
| glycerol-3P-acyltransferase | lipid metabolism |
| hydroxymethyl-glutaryl CoA reductase | mevalonic acid pathway |
| aminoacyl transferase | nucleic acid metabolism |
| transcription factors | nucleic acid metabolism |
| elongation factors | nucleic acid metabolism |

A suitable promoter-B is defined as a promoter that drives expression in substantially all cells wherein gene-A is expressed, with the proviso that it does not drive expression inside a nematode feeding structure, or not effectively. (With 'substantially all cells' is meant at least those cells that should be viable in order to get normal plant growth and or development required for commercial exploitation of such plants). As an illustration of plants in which the disruptive effect is not neutralized in exactly all cells of the host plant and which are nevertheless viable and suitable for commercial exploitation, those which express a disrupter gene according to this invention in stamen cells can be mentioned; this may yield male-sterile plants, which is even regarded as a commercially attractive trait in some crops. Suitable examples of the promoter-B type can be obtained from plants or plant viruses, or may be chemically synthesized. The regulatory sequences may also include enhancer sequences, such as found in the 35S promoter of CaMV (Kay et al., 1987, Science 236, 1299–1302), and mRNA stabilizing sequences such as the leader sequence of Alfalfa Mosaic Virus RNA4 (Brederode et al., 1980, Nucl. Acids Res. 8, 2213–2223) or any other sequences functioning in a like manner.

Alternatively, to provide for expression in all or effectively all plant tissues, a promoter-B/gene-B can be complemented with a second promoter-B'/gene-B having an expression pattern which is partly overlapping or entirely complementary to promoter-B/gene-B, with the proviso that neither promoter-B nor promoter-B' drives expression in the NFS. Also hybrid promoters, comprising (parts of) different promoters combined as to provide for the required expression pattern as defined herein, fall within the scope of the present invention.

Preferably, promoter-B is the Cauliflower Mosaic Virus 35S promoter or derivatives thereof, which is generally considered to be a strong constitutive promoter in plant tissues (Odell et al. 1985 Nature 313, 810–812). Another preferred example for promoter-B is the strong root promoter rolD (Leach & Aoyagi 1991 Plant Sci. 79; 69–76) from plasmid pRiA4 of *Agrobacterium rhizogenes*; the 5' flanking region of ORF15 (Slightom et al. 1986, J. Biol. Chem. 261, 108–121). The suitability of other constitutive promoters such as the nopaline synthase promoter (Bevan, 1984, Nucl. Acids Res. 12, 8711–8721) or figwort mosaic virus promoter (EP-A 426 641) for use as promoter-B can be tested through fusion to marker genes such as GUS (Jefferson, 1987, Plant Mol. Biol. Reporter 5, 387–405), transfer of these constructs to plants and histochemical analysis of such transgenic plants after infection with plant-parasitic nematodes (PPN).

Other regulatory sequences such as terminator sequences and polyadenylation signals include any such sequence functioning as such in plants, the choice of which is within the level of skill of the average skilled person in the art. An example of such sequences is the 3' flanking region of the nopaline synthase (nos) gene of *Agrobacterium tumefaciens* (Bevan, 1984, Nucl. Acids Res. 12, 8711–8721).

Further details of the two component approach can be found in WO93/10251 (herein incorporated by reference).

The choice of the plant species is primarily determined by the amount of damage through PPN infections estimated to occur in agriculture and the amenability of the plant species to transformation. Plant genera which are damaged during agricultural practice by PPN and which can be made significantly less susceptible to PPN by ways of the present invention include but are not limited to the genera mentioned in Table 2.

Nematode species as defined in the context of the present invention include all plant-parasitic nematodes that modify host cells into specially adapted feeding structures which range from migratory ectoparasites (e.g. Xiphinema spp.) to the more evolved sedentary endoparasites (e.g. Heteroderidae, Meloidogynae or Rotylenchulinae). A list of parasitic nematodes are given in Table 2, but the invention is not limited to the species mentioned in this table. More detailed listings are presented in Zuckerman et al. (eds., in: Plant Parasitic Nematodes, Vol. I 1971, New York, pp. 139–162).

TABLE 2

Examples of plant-parasitic nematodes and their principal host plants

| Nematode Species | Principal Host Plants |
| --- | --- |
| Meloidogyne | |
| M. hapla | wide range |
| M. incognita | wide range |
| M. exigua | coffee, tea, Capsicum, Citrullus |
| M. indica | Citrus |
| M. javanica | wide range |
| M. africana | coffee |
| M. graminis | cereals, grasses |
| M. graminicola | rice |
| M. arenaria | wide range |
| Heterodera & Globodera | |
| H. mexicana | *Lycopersicon esculentum*, Solanum spp. |
| H. punctata | cereals, grasses |
| G. rostochiensis | *Solanum tuberosum*, Solanum spp, *Lycopersicon esculentum* |
| G. pallida | *Solanum tuberosum* |
| G. tabacum | *Nicotiana tabacum*, Nicotiana spp. |
| H. cajani | *Cajanus cajan*, *Vigna sinensis* |
| H. glycines | *Glycine max*, Glycine spp. |
| H. oryzae | *Oryza sativa* |
| H. schachtii | Beta spp, Brassica spp, |
| H. trifolii | Trifolium spp. |
| H. avenae | cereals, grasses |
| H. carotae | *Daucus carota* |
| H. cruciferae | Cruciferae |
| H. goettingiana | *Pisum sativum*, Vicia spp. |

Within the context of this invention, a plant is said to show reduced susceptibility to plant parasitic nematodes if a statistically significant decrease in the number of mature females developing at the surface of plant roots can be observed as compared to control plants. Susceptible/ resistance classification according to the number of maturing females is standard practice both for cyst- and root-knot nematodes (e.g. Labondia, 1991, Plant Disease 75, 453–454; Omwega et al., 1990, Phytopathol. 80, 745–748).

A NFS according to the present invention shall include an initial feeding cell, which shall mean the cell or a very limited number of cells destined to become a nematode feeding structure, upon induction of the invading nematode.

A NFS disruptive substance according to the invention is not limited to have adverse effects on the NFS only; also disruptive effects are contemplated that, in addition, have an adverse effect on nematode development by way of direct interaction.

Several techniques are available for the introduction of recombinant DNA containing the DNA sequences as described in the present invention into plant hosts. Such techniques include but are not limited to transformation of protoplasts using the calcium/polyethylene glycol method, electroporation and microinjection or (coated) particle bombardment (Potrykus, 1990, Bio/Technol. 8, 535–542).

In addition to these so-called direct DNA transformation methods, transformation systems involving vectors are widely available, such as viral vectors (e.g. from the Cauliflower Mosaic Virus (CaMV) and bacterial vectors (e.g. from the genus Agrobacterium) (Potrykus, 1990, Bio/Technol. 8, 535–542). After selection and/or screening, the protoplasts, cells or plant parts that have been transformed can be regenerated into whole plants, using methods known in the art (Horsch et al., 1985, Science 225, 1229–1231). The choice of the transformation and/or regeneration techniques is not critical for this invention.

According to a preferred embodiment of the present invention use is made of so-called binary vector system (disclosed in EP-A 120 516) in which Agrobacterium strains are used which contain a helper plasmid with the virulence genes and a compatible plasmid, the binary vector, containing the gene construct to be transferred. This vector can replicate in both *E. coli* and in Agrobacterium; the one used here is derived from the binary vector Bin19 (Bevan, 1984, Nucl. Acids Res. 12, 8711–8721). The binary vectors as used in this example contain between the left- and right-border sequences of the T-DNA, an NPTII-gene coding for kanamycin resistance (Bevan, 1984, Nucl. Acids Res. 12, 8711–8721) and a multiple cloning site to clone in the required gene constructs.

Recent scientific progress shows that in principle monocots are amenable to transformation and that fertile transgenic plants can be regenerated from transformed cells. The development of reproducible tissue culture systems for these crops, together with the powerful methods for introduction of genetic material into plant cells has facilitated transformation. Presently, preferred methods for transformation of monocots are microprojectile bombardment of explants or suspension cells, and direct DNA uptake or electroporation (Shimamoto, et al., 1989, Nature 338, 274–276). Transgenic maize plants have been obtained by introducing the *Streptomyces hygroscopicus* bar gene, which encodes phosphinothricin acetyltransferase (an enzyme which inactivates the herbicide phosphinothricin), into embryogenic cells of a maize suspension culture by microparticle bombardment (Gordon-Karnn, 1990, Plant Cell, 2, 603–618). The introduction of genetic material into aleurone protoplast.,; of other monocot crops such as wheat and barley has been reported (Lee, 1989, Plant Mol. Biol. 13, 21–30). Wheat plants have been regenerated from embryogenic suspension culture by selecting only the aged compact and nodular embryogenic callus tissues for the establishment of the embiryogenic suspension cultures (Vasil, 1990 Bio/Technol. 8, 429–434). The combination with transformation systems for these crops enables the application of the present invention to monocots. These methods may also be applied for the transformation and regeneration of dicots.

The following examples are given only for purposes of illustration and do not intend to limit the scope of the invention.

EXPERIMENTAL PART

DNA Procedures

All DNA procedures were carried out according to standard methods described in Maniatis (Molecular Cloning, A laboratory Manual 2nd Edition, Cold Spring Harbor Laboratory, 1990).

Transformation of Arabidopsia

Transformation was carried out using co-cultivation of *Arabidopsis thaliana* (ecotype C24) root segments with Agrobacterium strain MOG101 containing a suitable binary vector as described by Valvekens et al. (1988, Proc. Nat. Acad. Sci. USA 85, 5536–5540) which is as follows:

Arabidopsis seeds were vernalized for 7 days at 4° C. before germination. Seeds were surface-sterilized for 2 min in 70% EtOH, transferred to 5% NaOCl/0.5% $NaDodSO_4$ for 15 min rinsed five times with sterile distilled water, and placed on 150×25 mm Petri dishes containing germination medium (GM) (Table 3) to germinate. Petri dishes were sealed with gas-permeable medical tape (Urgopore, Chenove France). Plants were grown at 22° C. in a 16-hr light/8-hr dark cycle. The same growth-room conditions were used for tissue culture procedures. All plant media were buffered with 2-(N-morpholino)ethanesulfonic acid at 0.5 g/liter (pH 5.7: adjusted with 1 M KOH), solidified with 0.8% Difco Bacto agar, and autoclaved at 121° C. for 15 min. Hormones and antibiotics were dissolved in dimethyl sulfoxide and water, respectively, and were added to the medium after autoclaving and cooling to 65° C.

Intact roots were incubated for 3 days on solidified 0.5/0.05 medium (Table 3). Roots were then cut into small pieces of about 0.5 cm (herein referred to as "root explants") and transferred to 10 ml of liquid 0.5/0.05 medium; 0.5–1.0 ml of an overnight Agrobacterium culture was added. The root explants and bacteria were mixed by gentle shaking for about 2 min.

Subsequently, the root explants were blotted on sterile filter paper to remove most of the liquid medium and cocultivated for 48 hr on 0.5/0.05 agar. The explants were then rinsed in liquid 0.5/0.05 medium containing 1000 mg of vancomycin (Sigma) per liter. The pieces were blotted and then incubated on 0.15/5 agar (Table 3) supplemented with 750 mg of vancomycin and 50 mg of Km per liter. Three weeks after infection with agrobacteria containing a chimeric neo gene, green Km-resistant (KmR) calli were formed in a background of yellowish root explants. At this point the root explants were transferred to fresh 0.15/5 agar containing only 500 mg of vancomycin and 50 mg of Km per liter. Three weeks later most green call had formed shoots. Transformed shoots were transferred to 150×25 mm Petri dishes containing GM to form roots or seeds or both. In these Petri dishes, many regenerants formed seeds without rooting. Rooted plants could also be transferred to soil to set seed. The following modification was made to obtain the initial root material 6 mg sterilized Arabidopsis thaliana C24 seeds were germinated in 50 ml GM (250 ml Erlenmeyer) on a rotary shaker (100 rpm) in a growth room for 9 days under low light conditions 3. Transgenic plants were regenerated from shoots grown on selection medium (50 mg/l kanamycin), rooted and transferred to germination medium or soil.

TABLE 3

Plant Media

| | | CIM | | | SIM | |
|---|---|---|---|---|---|---|
| | GM | R3* | PG1* | 0.5/0.05 | 0.05/7* | 0.15/5* |
| Salts + vitamins | MS | MS | B5 | B5 | MS | B5 |
| Sucrose, g/L | 10 | 30 | — | — | 30 | — |
| Glucose, g/L | — | — | 20 | 20 | — | 20 |
| IAA, mg/L | — | 5 | — | — | 0.05 | 0.15 |
| 2,4-D, mg/L | — | 0.5 | 2 | 0.5 | — | — |
| 2ipAde, mg/L | — | — | — | — | 7 | 5 |
| Kin, mg/L | — | 0.3 | 0.05 | 0.05 | — | — |

*L, liter; IAA, indole-3-acetic acid; Kin, kinetin; 2ipAde, $N^6$-(2-isopentenyl)adenine; CIM, callus-inducing medium; SIM, shoot-inducing medium; MS, Murashige & Skoog medium; B5, Gamborg B5 medium

Transformation of Potato

For the transformation of *Solanum tuberosum* var. Kardal a protocol as described in Hoekema et al. 1989 Bio/Technology 7, 273–278 was used with several modifications. Peeled surface-sterilized potato tubers were cut in 2 mm thick slices. These were used to cut out disks of 1 cm in diameter around the periphery of the slice. The disks were collected in WM (Murashige & Skoog medium, containing 1 mg/l thiamine HCl, 0.5 mg/l pyridoxine Hcl, 0.5 mg/l nicotinic acid, 100 mg/l myo-inositol, 30 g/l sucrose, 0.5 g/l MES pH 5.8). Inoculation with Agrobacterium tumefaciens strain EHA105 (Hood et al. 1993 Transgenic Research 2, 208–218) was done by replacing the WM with 100 ml fresh WM containing the resuspended pellet of 10 ml Agrobacterium culture grown freshly in LB+appropriate antibiotic to an $OD_{600}$ of 0.5–0.7. After incubating the tuber disks for 20 min in the bacterium suspension they were transferred to solidified CM (WM supplemented with 8 g/l agar, 3.5 mg/l zeatin riboside, 0.03 mg/l indole acetic acid) at a density of 20 explants/petridish. After two days the disks were transferred to PM (CM supplemented with 200 mg/l cefotaxime, 100 mg/l vancomycin) to select against the Agrobacteria. Three days later the disks were transferred to SIM plates (CM supplemented with 250 mg/l carbenicillin, 100 mg/l kanamycin) at a density of 10 explants/petridish to select for the regeneration of transformed shoots. After 2 weeks the tissue disks were transferred to fresh SIM, and after another 3 weeks they were transferred to SEM (SIM with 10×lower concentration of hormones). About 8–9 weeks after co-cultivation the shoots were large enough to cut them from the callus tissue and transfer them to glass tubes (Sigma, Cat.nr. C5916) containing 10 ml of RM (WM containing 0.5×MS salts, 0.5×vitamins, 10 g/l sucrose, 100 mg/l cefotaxime, 50 mg/l vancomycin and 50 mg/l kanamycin) for rooting maintenance in vitro and vegetative propagation.

Handling of Nematodes, Growth and Infection of Plant Roots

Arabidopsis seeds were surface sterilized and sown in petri dishes (φ:9 cm) on B5 medium containing 20 g/l glucose and 20 mg/l kanamycin. After 3 days at 4° C. the plates were incubated for 2 weeks in a growth chamber at 22° C. with 16-hr light/8 hr-dark cycle. Kanamycin-resistant plants were then transferred to soil-filled translucent plastic tubes (30×15×120 mm, Kelder plastibox b.v., The Netherlands). The tubes were placed tilted at an angle of 60 degrees to the vertical axis causing the roots to grow on the lower side of the tubes. This allows to monitor the infection process by eye and facilitates removal of the root system from the soil for GUS analysis. Infection was done after two more weeks by injecting a suspension containing 500 second stage larvae of *Heterodera schachtii* (in 3 ml $H_2O$) per root system or 300 second stage larvae of *Meloidogyne incognita* per root system into the soil.

Similarly, transformed potato shoots which had rooted on kanamycin-containing RM medium were transferred to soil-filled translucent plastic tubes (30×15×120 mm, Kelder plastibox b.v., The Netherlands) and grown tilted for another 2 weeks at 22° C. with 16 h light/8 h dark cycle. Infection was done by injecting a suspension containing 500 second stage larvae of *Globodera pallida* (in 3 ml $H_2O$) per root system into the soil.

GUS Assay

GUS activity was determined at various times during the infection process by thoroughly washing the root systems to remove most of the adhering soil and incubating them in X-Gluc solution (1 mg/ml X-Gluc, 50 mM $NaPO_4$ (pH7), 1 mM $K_4Fe(CN)_6$, 1 mM K $K_3Fe(CN)_6$, 10 mM EDTA, 0.1% Triton X100) at 37° C. over night. After removal of the chlorophyll from the tissue by incubation with 70% ethanol for several hours GUS staining was monitored under the microscope.

DNA Sequence Determination

Sequencing was done using standard techniques known to persons skilled in the art.

EXAMPLE 1

Construction of Binary Vector pMHOG800

Figure 2:
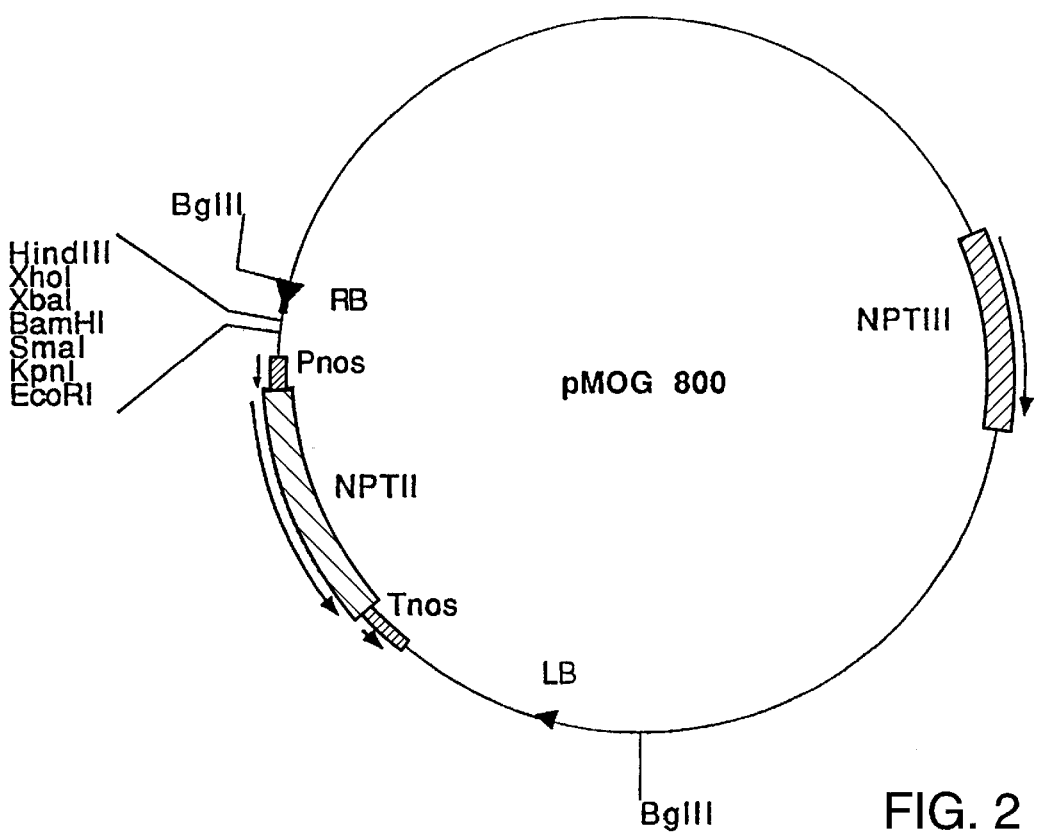
FIG. 2. Schematic plasmid map of Binary vector pMOG800.

The binary vector pMOG800 is a derivative of pMOG23 (FIG. 1, deposited at the Centraal Bureau voor schimmelcultures, Oosterstraat 1, Baarn, The Netherlands on Jan. 29, 1990 under number CBS 102.90) in which an additional KpnI restriction site was introduced into the polylinker between EcoRI and SmaI. This plasmid contains between the left and right borders of T-DNA a kanamycin resistance gene for selection of transgenic plant cells (FIG. 2). A sample of *E. coli* DH5 alpha, harbouring PMOG800, was deposited at the Centraal Bureau voor Schimmelcultures, Oosterstraat 1, Baarn, The Netherlands, on Aug. 12, 1993 under number CBS 414.93.

EXAMPLE 2

Construction of Promoterless GUS Construct pMOG553

Figure 3:
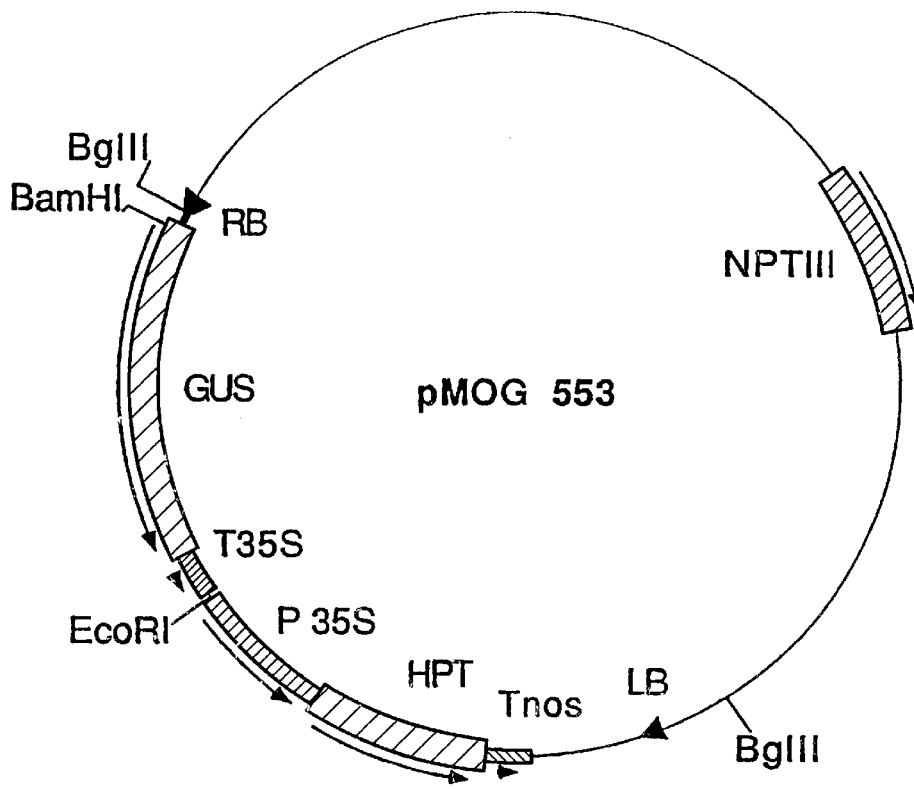
FIG. 3. Schematic plasmid map of Binary vector pMOG553.

Construction of this vector is described in Goddiin et al. 1993 Plant J 4, 863–873. In this reference an error occurs; the construct contains a CaMV 35S RNA terminator behind the β-glucuronidase gene instead of the indicated nos terminator. The sequence between the T-DNA borders of this binary vector is available from the EMBL database under accession number: X84105. pMOG553 carries the HygR marker for plant transformation (FIG. 3).

EXAMPLE 3

Identification and Isolation of a Trapped NFS-preferential Promoter Fragment in *Arabidopsis thaliana*

The binary vector pMOG553 was mobilized by triparental mating to *Agrobacterium tumefaciens* strain MOG101 which is described in detail in WO 93/10251. The resulting strain was used for Arabidopsis root transformation. More than 1100 transgenic Arabidopsis plant lines were obtained in this way. Transgenic plants were grown to maturity, allowed to self-fertilize and the resulting seeds (S1) were harvested and vernalized. Subsequently S1 seeds were germinated on nutrient solution (Goddijn et al. 1993 Plant J 4, 863–873) solidified with 0.6% agar, 10 mg/l hygromycin and stored at 4° C. for a 4 day imbibition period. At day 5 the plates were transferred to room temperature and moderate light (1000 lux, 16 h L/8 h D) for germination. Fourteen days old seedlings were transferred to potting soil in tilted translucent plastic tubes (30×15×120 mm) for further growth at 5000 lux (20° C.). Growing the plants in this way causes most of the root system to grow on the lower side of the tubes in the interphase between soil and tube. After two weeks the roots were infected with nematodes as described in the Experimental part. At several time points after inoculation (ranging from 2–14 days), the root systems were analyzed for GUS activity as described in the Experimental part. Line pMOG553#25 was identified as a line which showed rather strong GUS expression inside syncytia and giant cells induced by *Heterodera schachtii* and *Meloidogyne incognita*, respectively. In uninfected control plants (as well as in the infected plants) of this line very weak GUS expression was detected in the vascular cylinder at the base and at the tip of young lateral roots and in various green parts of the plant.

Line pMOG553#25 was found to segregate at a 1:3 ratio, indicating that the GUS construct is present at one locus in the genome. By Southern analysis four different, presumably linked, T-DNA copies were identified. In order to determine which of the four plant sequences flanking the right T-DNA borders conferred GUS expression in syncytia, a library was constructed from genomic DNA of line pMOG553#25. The DNA was partially digested with SauIIIa and after partially filling in the overhanging site with the nucleotides T and C the fragments were ligated in XhoI-digested lambdaGEM11 arms, where the restriction sites had also been partially filled with the nucleotides G and A. The partial filling makes the SauIIIa site compatible with XhoI and prevents the cloning of multiple inserts in the lambda vector.

Circa 300.000 recombinant phages were screened with a gusA probe. Restriction analysis and partial sequencing of positive clones resulted in the isolation of clones representing all four T-DNA insertion sites, tag1–tag4. The following RB flanking subfragments were cloned in front of gusA in pMOG819, a 4.0 kb SmaI fragment of tag 1 resulting in pMOG821, a 1.2 kb BamHI fragment of tag 2 resulting in pMOG820, a 1.6 kb SmaI fragment of tag 3 resulting in pMOG847 and a 2.7 kb BamHI fragment of tag 4 resulting in pMOG848. In the constructs pMOG820, pMOG821, pMOG847 and pMOG848 the exact sequence context between the gusA gene and the flanking plant sequence was retained, since both BamHI and SmaI cleave in the original tagging vector pMOG553 between the right T-DNA border and the gusA coding region.

EXAMPLE 4

Construction of Promoterleas GUS Construct pMOG19

Figure 4:
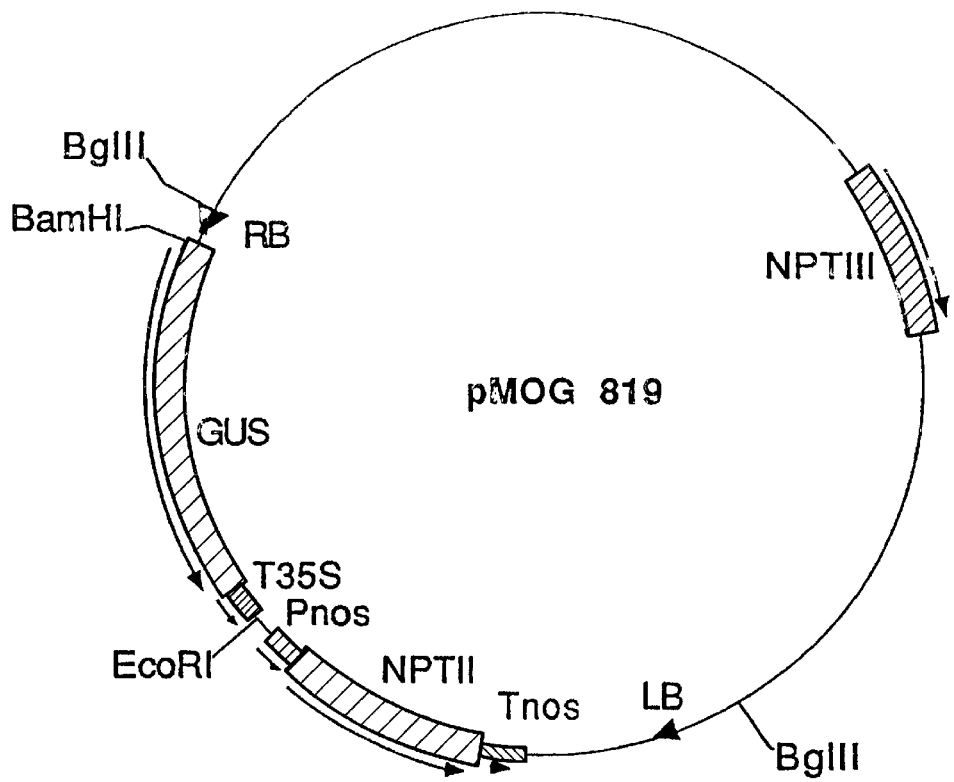
FIG. 4. Schematic plasmid map of Binary vector pMOG819.
Figure 5:
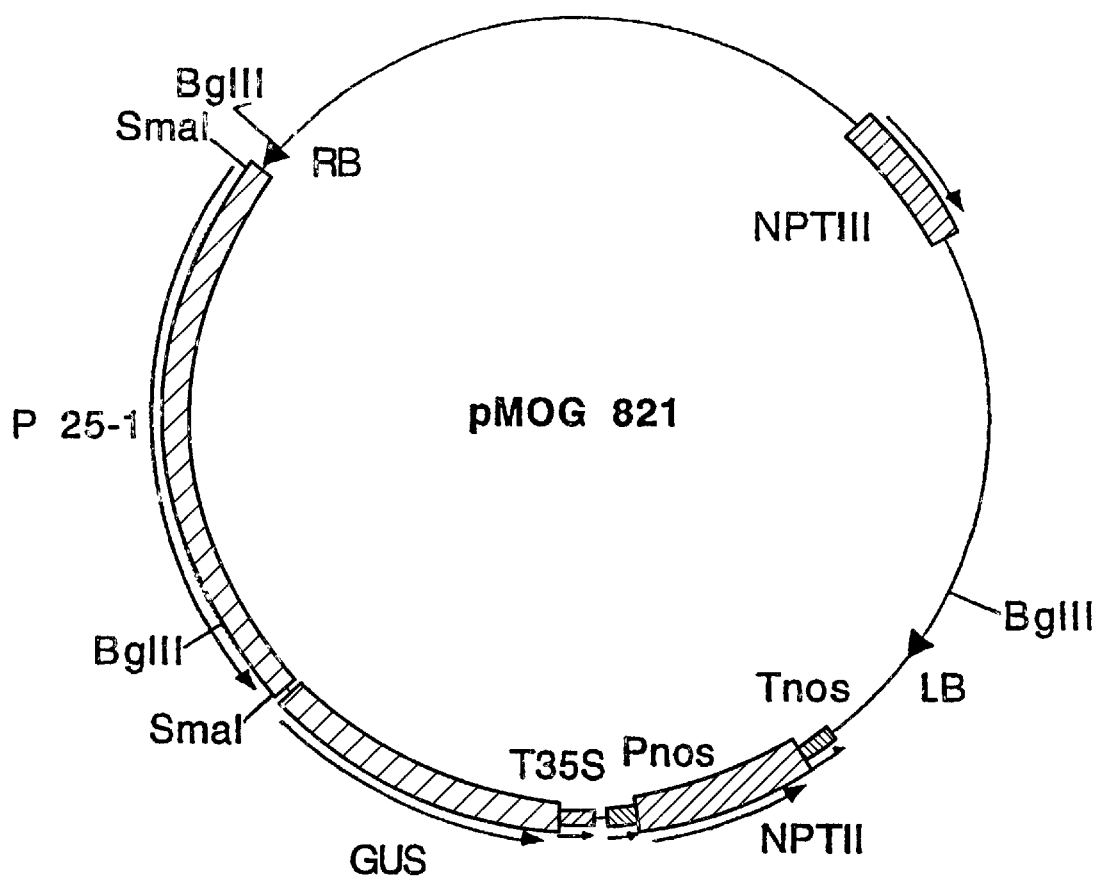
FIG. 5. Schematic plasmid map of Binary vector pMOG821.

This vector was constructed by cloning the GUSintron coding region (Varicanneyt et al. 1990, Mol. Gen. Genet. 220; 245–250) of pMOG553 as a BamHI-EcoRI fragment in the polylinker of pMOG800. The binary vector pMOG819 (FIG. 4) serves to introduce the cloned promoter fragments for further expression analysis after transformation of plants.

EXAMPLE 5

Analysis of Promoter Fragments after Re-introduction into Arabidopsias

To determine the tissue-specific activity of the cloned promoter fragment the resulting clones pMOG820, pMOG821, pMOG847 and pMOG848 were mobilised to *Agrobacterium tumefaciens* and the corresponding strain was used to transform wildtype *Arabidopsis thaliana* plants. Per construct 19–31 transformants were produced. Seeds from the primary transformants were harvested and grown up for infection assays with *Heterodera schachtii* as described in the Experimental part. GUS analysis after nematode infection showed that only plants transformed with pMOG821 (tag1) expressed the reporter gene in syncytia.

Figure 6:
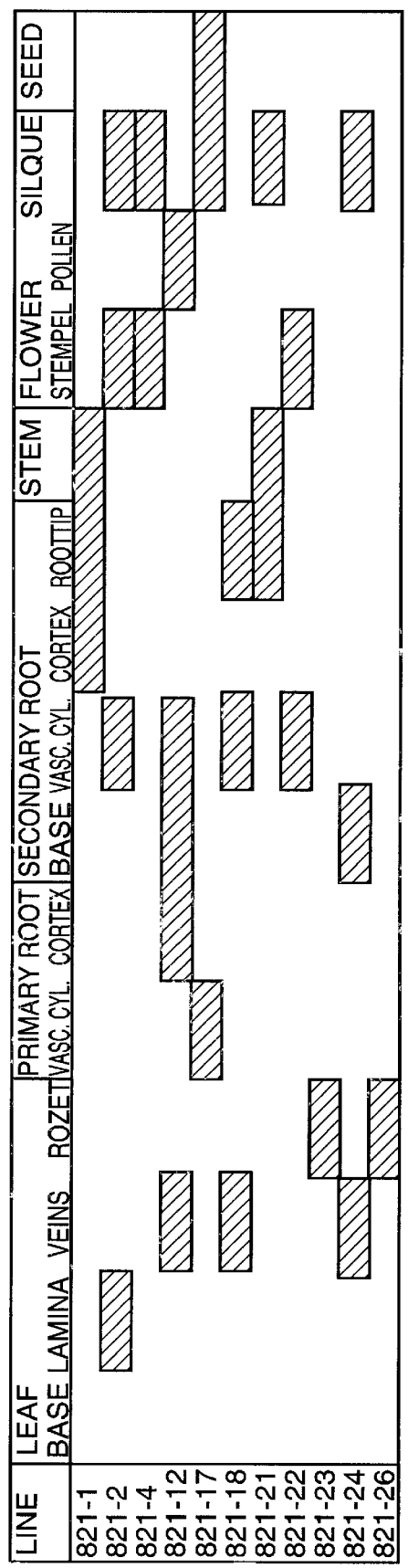
FIG. 6. Expression patterns outside the NFS of several pMOG821 transformed *Arabidopsis thaliana* lines.
Figure 7:
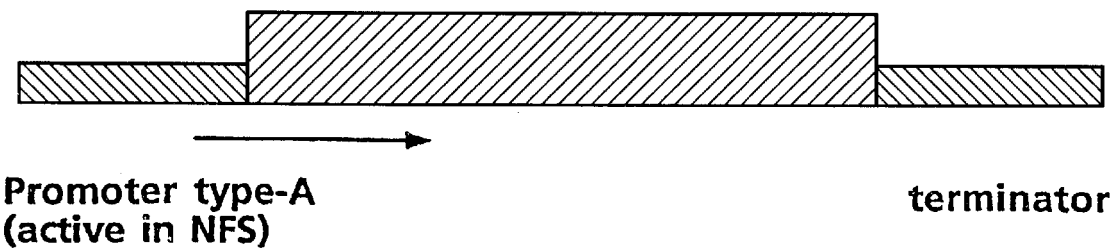
FIG. 7. Schematic representation of a NFS disrupter gene and a neutraliser gene in a two component system for engineering of nematode resistant plants FIG. 8. Schematic plasmid map of Binary vector pMOG944.
Figure 7:
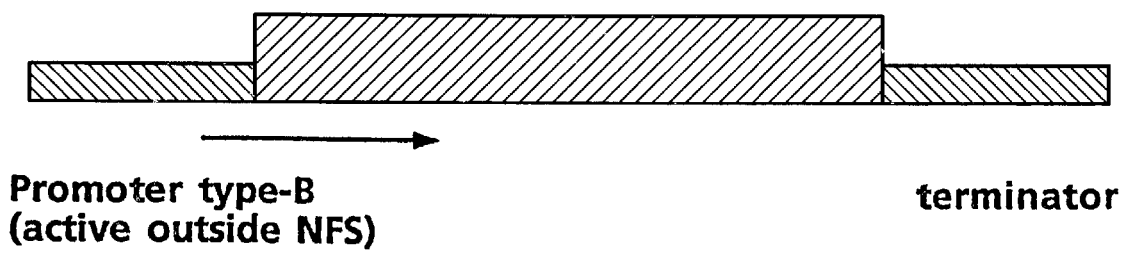
Figure 8:
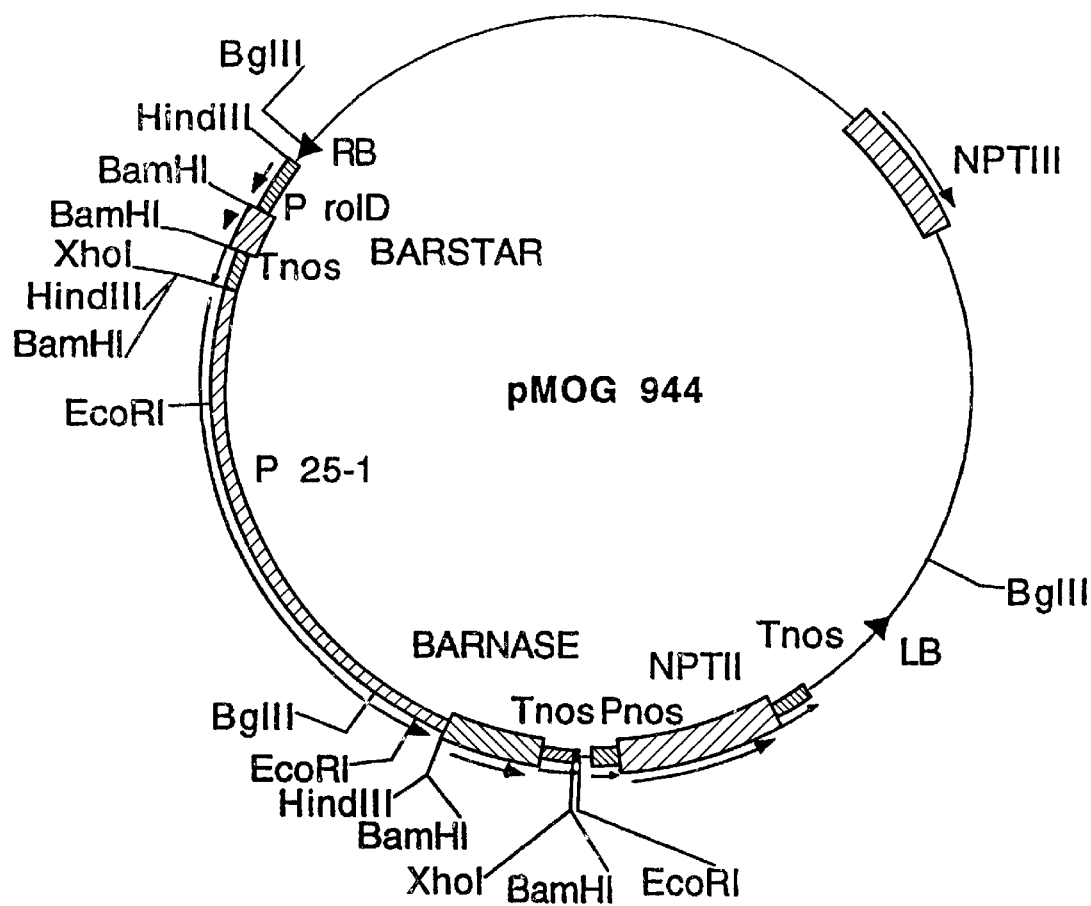

This result proves that plant sequences flanking the right border of tag 1 (subsequently referred to as #25.1) confer GUS expression in syncytia. This expression was found in 21 out of 29 pMOG821 lines tested. Some weak expression was also found in parts of the vascular tissue of lateral roots and in some aerial plant tissues. GUS expression outside the syncytium showed strong variation from line to line. (see FIG. 6).

Even though this side activity was generally much weaker than the GUS-activity inside syncytia, none of the syncytium-positive lines was entirely specific for the feeding sites.

GUS-expression was also found in giant cells induced by infection with *Meloidogyne incognita* in the same lines which expressed GUS in syncytia induced by *Heterodera schachtii*. This shows that the #25.1 sequence can be used as a nearly feeding site specific promoter to engineer plants having reduced susceptibility to *Meloidogyne incognita* and *Heterodera schachtii*.

During the tissue culture phase, it was observed that the #25.1 regulatory sequence was also active as a promoter, thus prompting the need to use a neutralizing gene if the #25.1 promoter fragment is transferred to Arabidopsis with a plant cell disruptive gene under its control, such as barnase (see Example 7 and 8).

EXAMPLE 6

Sequence Determination of Promoter Tags 1–4 from Line pMOG553#25

The plant sequences flanking the right T-DNA borders of tag 2–4 were partially determined. The 4kb SmaI fragment of tag 1 was sequenced entirely. The sequence revealed that the most distal (5') 0.5 kb of this sequence were derived from the lambda vector, leaving 3484 bp of plant promoter sequence. Sequencing was done using the primer walking strategy on CsCl purified DNA, with the automatic sequencer ALF of Pharmacia. Fluor dATP was used in combination with the AutoRead sequencing kit. The procedure is described in Voss et al. (1992) Mol Cell Biol 3,153–155. The sequence is depicted in SEQ ID NO: 1.

EXAMPLE 7

Cloning of #25.1 in front of barnase

A fragment containing the barnase coding region was PCR amplified from pMT416 (Hartley (1988) J Mol Biol 202, 913–915) using primers 5' CGGACTCTGGATCCG-GAAAGTG 3' (SEQ ID NO: 3) and 5' CTGCTCGAGC-CTAGGCACAGGTTATCAACACGTTTG 3' (SEQ ID NO: 4). These primers introduce flanking BamHI and XhoI restriction sites to facilitate cloning of the fragment. The fragment was cloned upstream of a nopaline terminator sequence in a vector containing an additional barstar gene under control of a Taq promoter (necessary to overcome toxicity of barnase in bacteria). To eliminate toxicity of barnase expression in subsequent cloning steps a ST-LS1 intron was inserted in the StyI site of barnase. An NcoI site was created at the barnase translation initiation codon by recombinant PCR using the primers 5' CGGACTCTG-GATCCGGAAAGTG 3' (SEQ ID NO: 3) and 5' CTTACTC-GAGCCATGGTAAGTTTCTGC 3' (SEQ ID NO: 5), resulting in pOG16.1. Subsequently the BamHI site flanking the barnase coding region was destroyed by cleaving pOG16.1 with BamHI, polishing the overhanging ends with Klenow polymerase and religation, resulting in pFL17. The 5' untranslated sequence of barnase was further modified to resemble the corresponding sequence in the original line pMOG553#1164 by annealing the following oligonucleotides 5' GATCTAGACTCGAGAAGCTTGGATC-CCCGGGTAGGTCAGTCCCC 3' (SEQ ID NO: 6) and 5' CATGGGGGACTGACCTACCCGGGGATC-CAAGCTTCTCGAGTCTA 3' (SEQ ID NO: 7), and litigating the resulting adapter between the BglII site and the NcoI site of pOG16.1, resulting in clone pFL18. The 4kb promoter from line 25 tag 1 was cloned out of pMOG821 as a BamHI fragment and inserted in the unique BamHI site of clone pFL18 immediately 5' of the barnase coding region, restoring the original sequence context of line 25 up to the barnase translation initiation codon, resulting in pFL38.

EXAMPLE 8

Construction rolD-B*

Construct pFL11 contains a chimeric barstar gene in a binary vector. This construct was cloned in the following way. The barstar coding region resides on a HindIII/BamHI fragment in construct pMT316 (Hartley (1988) J Mol Biol 202,913–915). The HindIII site was changed into a BamHI site by ligating in this site the self-annealing adapter 5' AGCTCGGATCCG 3' (SEQ ID NO: 8). Subsequently, the resulting BamHI fragment was cloned between a double enhanced CaMV 35S promoter and a nos terminator in the expression cassette pMOG180, described in WO93/10251, resulting in pOG30. Using the adapter 5' GGCTGCTC-GAGC 3' (SEQ ID NO: 9) the HindIII site at the 3' end of the nos terminator was changed into an XhoI site and the EcoRI site at the 5' end of the promoter was changed into a HindIII site using the adapter 5' AATTGACGAAGCT-TCGTC 3' (SEQ ID NO: 10). Then the 35S promoter was replaced by the promoter from the *Agrobacterium rhizogenes* RolD gene. This promoter was excised as a HindIII/BamHI fragment from construct pDO2, obtained from F. Leach (Leach and Aoyagi (1991) Plant Sci 79, 69–76). From the resulting clone, pOG38, the barstar gene including promoter and terminator was excised by digestion with HindIII and XhoI and inserted in the respective sites of the polylinker in pMOG800, resulting in pFL11.

EXAMPLE 9

Transformation of Potato Plants with pMOG944 and Testing for Increased Resistance Against *Globodera pallida*

The binary vector pMOG944 was mobilised to *Agrobacterium tumefaciens* and the resulting strain was used for transformation of tuber discs from the potato cultivar Kardal as described in the Experimental part. A total of 80 transgenic lines were obtained. These lines were propagated vegetatively by cutting shoots in segments containing at least one node and rooting them in vitro. Per line 15 plants are tested for increased resistance to *Globodera pallida* as described in the Experimental part. It is expected that potato plants transformed with the pMOG944 contained Barneise/Barstar construct show reduced susceptibility to *Globodera pallida* due to the nematode-induced expression of Barnase inside the (developing) nematode feeding structure.

The above examples merely serve to illustrate the invention and are not meant to indicate its limits. Numerous modifications will readily occur to the person skilled in the art which are within the scope of the invention.

What is claimed is:

1. An isolated promoter sequence capable of promoting root knot and cyst nematode-inducible transcription of a heterologous DNA sequence operably linked thereto when introduced into a plant, wherein said promoter sequence comprises the nucleotide sequence represented as SEQ ID No. 1.

2. An isolated promoter sequence capable of promoting root knot and cyst nematode-inducible transcription of a heterologous DNA sequence operably linked thereto when introduced into a plant, wherein said promoter sequence comprises a fragment of the nucleotide sequence represented as SEQ ID No. 1 having said promoter active.

3. A chimeric DNA construct comprising in the direction of transcription the isolated promoter sequence according to claim 1 and a heterologous DNA sequence to be expressed under the transcriptional control of said promoter sequence.

4. The chimeric DNA construct according to claim 3, wherein the heterologous DNA sequence encodes an RNA.

5. The chimeric DNA construct according to claim 4 wherein said RNA is in antisense orientation.

6. The chimeric DNA construct according to claim 4 wherein the RNA encodes a protein which is toxic or detrimental to a plant parasitic nematode.

7. The chimeric DNA construct according to claim 6, wherein the encoded protein is barnase.

8. A replicon comprising the chimeric DNA construct according to claim 3.

9. A replicon comprising in the direction of transcription the promoter sequence according to claim 1 and at least one recognition site for a restriction endonuclease for insertion of a heterologous DNA sequence to be expressed under the control of said promoter sequence.

10. A micro-organism containing the replicon according to claim 8.

11. A plant cell having incorporated into its genome the chimeric DNAk construct according to any one of claims 3–7.

12. A root system of a plant comprising the plant cell according to claim 11.

13. A plant produced by grafting a plant onto the root system according to claim 12.

14. A plant comprising the plant cell according to claim 11.

15. A plant according to claim 14, wherein said plant is a dicotyledenous plant.

16. A plant according to claim 15, wherein said dicotyledenous plant is a potato plant.

17. A part of a plant selected from the group consisting of seeds, flowers, tubers, roots, leaves, fruits, pollen and wood, obtained from the plant according to claim 14, wherein the plant part comprises the plant cell according to claim 11.

18. A method of increasing a plant's resistance to a plant parasitic nematode, said method comprising the steps of:

(a) introducing into plant cells the chimeric DNA construct according to claim 3, (b) regenerating plants therefrom; and (c) selecting from the population of regenerated plants those plants having increased resistance to a plant parasitic nematode.

19. A process for identification of fragments having promoter activity in a plant, said process comprising the steps of:

(a) providing the isolated promoter sequence according to claim 1;

(b) generating fragments of the promoter sequence of step (a);

(c) transforming plants with the fragments of step (b) operably linked to a heterologous DNA sequence encoding a protein; and (d) identifying the fragments of step (b) having promoter activity in a plant by expression of the heterologous DNA sequence.

20. A process for transforming plants, said process comprising the steps of:

(a) providing the chimeric DNA construct according to claim 3; and (b) introducing said chimeric DNA construct into a suitable plant host.

21. A process for making a hybrid DNA regulatory promoter sequence, said process comprising the steps of:

(a) providing at least the isolated promoter sequence according to claim 1 or a fragment thereof having promoter activity in a plant; and (b) introducing said isolated promoter sequence or said fragment or a combination of said fragments with another DNA regulatory sequence to form a hybrid DNA regulatory promoter sequence.

* * * * *

UNITED STATES PATENT AND TRADEMARK OFFICE
CERTIFICATE OF CORRECTION

PATENT NO.    : 6,395,963 B1
DATED         : May 28, 2002
INVENTOR(S)   : Stephan Andreas Ohl et al.

It is certified that error appears in the above-identified patent and that said Letters Patent is hereby corrected as shown below:

Column 21,
Line 54, in the claim term "chimeric DNAk construct", "DNAk" should be changed to -- DNA --;

Column 22,
Line 54, in the claim term "DNA regulatory promoter sequence", the word "promoter" should be deleted to read -- DNA regulatory sequence --;
Line 61, in the claim term "DNA regulatory promoter sequence", the word "promoter" should be deleted to read -- DNA regulatory sequence --.

Signed and Sealed this

Thirteenth Day of August, 2002

Attest:

JAMES E. ROGAN
Attesting Officer                    Director of the United States Patent and Trademark Office